United States Patent [19]

McGredy

[11] Plant 4,385

[45] Feb. 27, 1979

[54] ROSE PLANT

[76] Inventor: Samuel D. McGredy, P.O. Box 14-100, Auckland, New Zealand

[21] Appl. No.: 874,824

[22] Filed: Feb. 3, 1978

[51] Int. Cl.[2] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A novel miniature rose characterized by medium sized exhibition-style yellow blooms of yellow coloring borne on a vigorous, free-branching plant.

2 Drawing Figures

The present invention relates to a new and distinct variety of rose plant of the miniature rose class, which was originated by my crossing as seed parent a seedling of a cross of "New Penny" × "Banbridge" and a seedling of a cross of "Border Flame" × "Manx Queen" as pollen parent.

Among the novel characteristics possessed by this new variety which distinguish it from its parents and all other varieties of which I am aware are : (1) high centered blooms of yellow coloring with slight cerise edging of outer petals borne singly and in small clusters, (2) flowers of many petals opening from long pointed buds with sepals of double bud length and (3) a vigorous, uniform branching, compact, spreading plant. Asexual reproduction by budding of the new variety as performed in Clackamas County, Oregon, shows that the foregoing and other distinguishing characteristics come true to form and are established and transmitted through succeeding propagations.

The new and improved rose variety which I have developed is an unusually fine miniature rose of yellow coloring, producing both singly-borne blooms and small clusters of high centered, hybrid-tea like form displayed on a vigorous, uniform branching plant. The flowers open flat with petals reflexing such that the blooms become star-shaped at maturity. Despite relatively heavy petalage (nominally 35 petals), the blooms open well and with slight lightening of outer petals. The bud form is also distinctively attractive both before showing color when sepals predominate; and upon opening when the cerise shading on outer petals is most visible. The plant is attractive in combining abundant waxy appearing foliage with well branching growth.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "12B" is plate 12B of the Royal Horticultural Society Color Chart.

Parentage: Seedling.

*Seed parent.*—Seedling of "New Penny" × "Banbridge".

*Pollen parent.*—Seedling of "Border Flame" × "Manx Queen".

Class: Miniature.

The following observations are made of specimens grown in Clackamas County, Oregon during the month of October.

1. FLOWER

Blooming Habit: Continuous.

A. Bud:

(1) *Size.*—Medium (1 to 1¼ inches).

(2) *Form.*—High centered.

(3) *Color.*—When sepals first divide — 12B tinted 43B on edges. When petals begin to unfurl — 12A tinted 43B on edges of first row of petals. When half-blown — 12B. Reverse side of petals — 12C.

(4) *Sepals.*—Long, pointed, extending about twice the length of bud (before opening), glabrous outside, downy inside with bract-like appendages near base.

(5) *Peduncle.*—Length — long. Aspect — straight. Strength — erect (strong). Color — 175B.

B. Bloom:

(1) *Size.*—Average size when fully expanded — about 1 to 1½ inches.

(2) *Borne.*—Singly and in small clusters on basal shoots.

(3) *Form.*—High centered blooms, becoming flat upon opening, petals reflexing crisply outward becoming pointed at maturity.

(4) *Petalage.*—Number of petals under normal conditions — about 35.

(5) *Color (during first two days).*—Inner petals at center of flower — 12B. Outer petals — 12D. Base of petals (point of attachment) — 12A. Reverse of petals — 12C. General tonality from a distance — maize yellow with early pink markings in bud becoming virtually obscured.

(6) *Color change.*—As bloom ages — little fading except at outer petals, with general tonality changing from 12C to 12D after three or more days. Stamens become evident at the bloom's full-blown stage.

C. Petals:

(1) *Texture.*—Crisp with good substance, stiff, paper-like.

(2) *Appearance.*—Top — satiny; reverse — flat.

(3) *Form.*—Elongate, obovate, mucronate.

(4) *Arrangement.*—Regularly arranged, shingle-like.
(5) *Petaloids in center.*—Few.
(6) *Persistence.*—Persistent, abscission in total from base of peduncle.
(7) *Fragrance.*—Slight, spicy.
(8) *Lasting quality.*—Very good on plant and as cut flower.

2. REPRODUCTIVE ORGANS

A. Stamens, filaments and anthers:
(1) *Arrangement.*—Regularly arranged, filaments short.
(2) *Color.*—12A.
B. Pollen: Color — 168B.
C. Styles: Even, bunched, short, numerous.
D. Stigmas: Color — surface 12B.
E. Hips: Ovoid, 6 to 8mm, color — 153D, seeds do not protrude.

3. PLANT

A. Form: Compact, spreading.
B. Growth: Vigorous, free and uniform branching, attaining height about 16 inches.
C. Foliage: Three and mostly five-leaflet leaves.
(1) *Size.*—Medium.
(2) *Quantity.*—Abundant.
(3) *Color.*—New foliage: upper side — near to 147A; under side — near to 146A. Old foliage: upper side — near to 139A; under side — near to 139B.
(4) *Shape.*—Oval, long pointed.

(5) *Texture.*—Upper side — shiny waxy. Under side — dull, flat.
(6) *Edge.*—Serrated.
(7) *Serration.*—Fine.
(8) *Leaf Stem.*—Color — near to 146A. Under side — 139B (rachis thornless).
(9) *Stipules.*—Very long almost to first leaflet, slight pointed beard.
(10) *Resistance to Disease.*—Blackspot — excellent. Mildew — good. Rust — excellent.
D. Wood:
(1) *New wood.*—Color — near 183A. Bark — smooth, shiny.
(2) *Old Wood.*—Color — 138A. Bark — smooth, shiny.
E. Thorns:
(1) *Thorns.*—Quantity: ordinary on main stalks, numerous on laterals; narrow, long pointed form; large; color when young — 183A; regularly positioned.
(2) *Prickles.*—None or rare.
F. Winter hardiness: Hardy.

I claim:

1. A new and distinct variety of rose plant of the miniature class, substantially as shown and described, characterized particularly by high centered, recurrent flowers of yellow coloring borne singly and in small clusters, opening from long pointed buds with long sepals displaying cerise shading upon showing color, produced on a vigorous, branching plant with abundant, shiny, waxy foliage.

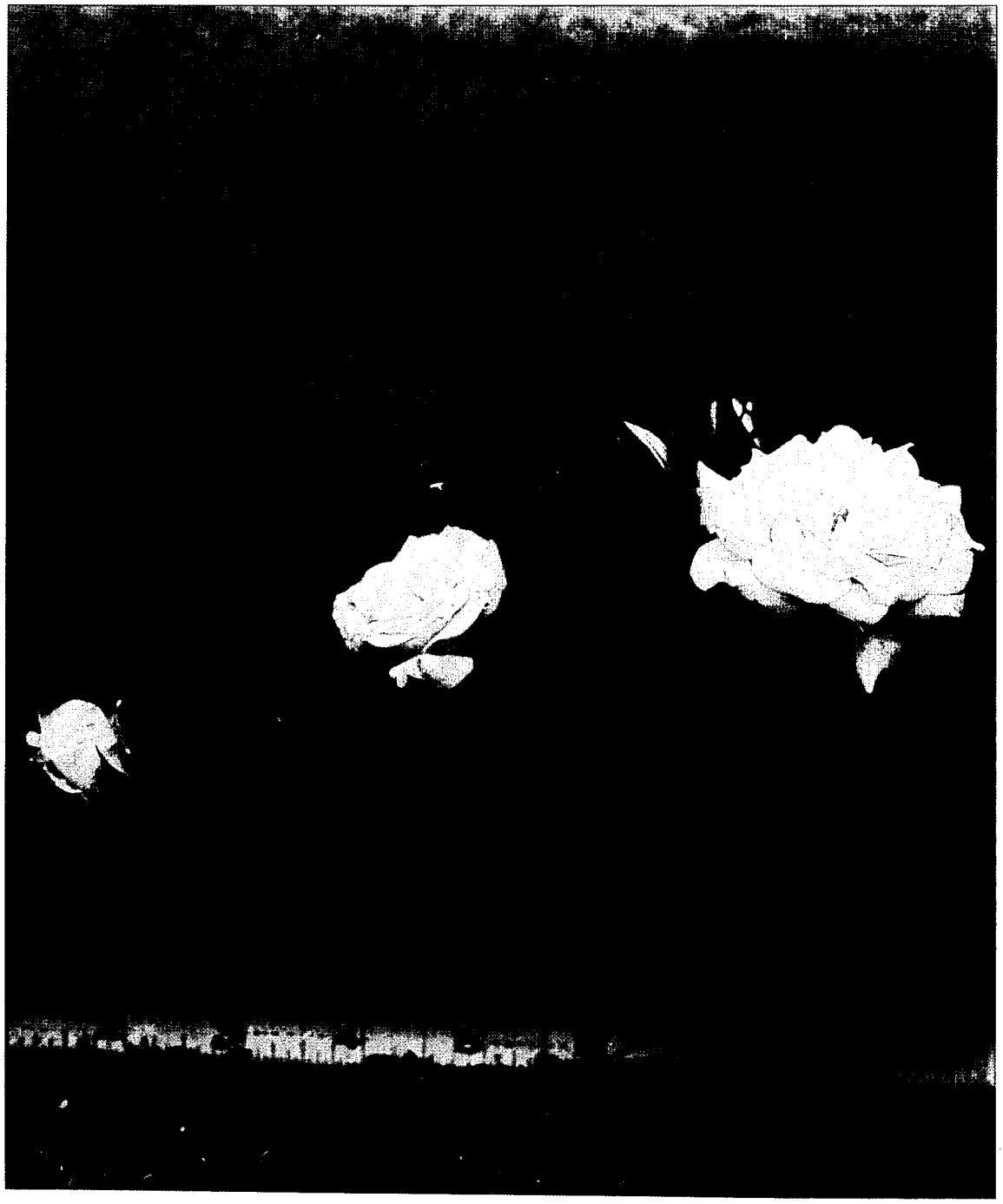

* * * * *